(12) United States Patent
Durling et al.

(10) Patent No.: US 9,339,364 B2
(45) Date of Patent: May 17, 2016

(54) INTRAVAGINAL DEVICE WITHDRAWAL ASSEMBLY

(71) Applicant: The Procter & Gamble Company, Cincinnati, OH (US)

(72) Inventors: Evan Joseph Durling, West Chester, OH (US); Kevin Charles Strong, Loveland, OH (US); Robert Clark Avery, Jr., Mason, OH (US); Hinrich Knuth, Mason, OH (US); Daniel Christy Jones, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 233 days.

(21) Appl. No.: 13/648,662

(22) Filed: Oct. 10, 2012

(65) Prior Publication Data
US 2014/0100417 A1    Apr. 10, 2014

(51) Int. Cl.
*A61F 6/06* (2006.01)
*A61F 2/00* (2006.01)
*A61F 6/08* (2006.01)
*A61F 6/12* (2006.01)

(52) U.S. Cl.
CPC . *A61F 2/005* (2013.01); *A61F 6/08* (2013.01); *A61F 6/12* (2013.01)

(58) Field of Classification Search
CPC ............... A61F 2/0045; A61F 2/0063; A61F 2230/0067; A61F 2250/0007; A61F 2220/0016; A61F 2250/0031; A61F 2250/0051; A61F 2002/041; A61F 2/02; A61F 2250/0067; A61F 2250/0068; A61F 2/0077

USPC .............. 128/830–841; 604/106, 285
See application file for complete search history.

(56) References Cited

U.S. PATENT DOCUMENTS

| | | | |
|---|---|---|---|
| 395,008 A | | 12/1888 | Sharp |
| 1,884,089 A | | 10/1932 | Millner |
| 2,638,093 A | | 5/1953 | Kulick |
| 3,431,905 A | * | 3/1969 | Davis et al. .................. 128/839 |
| 3,490,456 A | * | 1/1970 | Kortum ......................... 604/106 |
| 3,780,730 A | | 12/1973 | Weisman |
| 3,952,734 A | * | 4/1976 | Van Os et al. ................. 128/840 |
| 4,307,716 A | | 12/1981 | Davis |
| 5,045,079 A | | 9/1991 | West |
| 5,269,321 A | | 12/1993 | MacDonald et al. |
| 5,417,226 A | | 5/1995 | Juma |
| 5,483,832 A | | 1/1996 | Pauser et al. |
| 5,618,256 A | | 4/1997 | Reimer |
| 6,039,828 A | | 3/2000 | Achter et al. |
| 6,090,038 A | | 7/2000 | Zunker et al. |
| 6,090,098 A | | 7/2000 | Zunker et al. |
| 6,142,928 A | | 11/2000 | Zunker et al. |
| 6,458,072 B1 | | 10/2002 | Zunker |
| 6,478,726 B1 | | 11/2002 | Zunker |
| 6,558,370 B2 | | 5/2003 | Moser |
| 6,635,800 B2 | | 10/2003 | Jackson et al. |
| 6,645,136 B1 | | 11/2003 | Zunker et al. |
| 6,679,831 B1 | | 1/2004 | Zunker et al. |
| 6,695,763 B2 | | 2/2004 | Zunker et al. |
| 6,723,031 B1 | | 4/2004 | Wild |
| 6,773,423 B2 | | 8/2004 | Osborn et al. |
| 6,824,536 B2 | | 11/2004 | Randall et al. |
| 6,932,805 B2 | | 8/2005 | Kollwitz et al. |

(Continued)

*Primary Examiner* — Michael Brown
(74) *Attorney, Agent, or Firm* — Andres E. Velarde (57) ABSTRACT

An intravaginal device having an aperture and a withdrawal assembly. The withdrawal assembly has a withdrawal member and an obstruction.

19 Claims, 9 Drawing Sheets

(56) References Cited

U.S. PATENT DOCUMENTS

| | | |
|---|---|---|
| 7,056,278 B2 | 6/2006 | Adamkiewicz |
| 7,160,279 B2 | 1/2007 | Pauley et al. |
| 7,628,156 B2 | 12/2009 | Astani et al. |
| 7,673,631 B2 | 3/2010 | Astani et al. |
| 7,779,843 B2 | 8/2010 | Astani et al. |
| 8,568,374 B2 * | 10/2013 | De Graaff et al. ............ 604/285 |
| 2002/0120246 A1 | 8/2002 | Buzot |
| 2002/0143303 A1 | 10/2002 | Intravartolo et al. |
| 2003/0130637 A1 | 7/2003 | Intravartolo et al. |
| 2005/0096621 A1 | 5/2005 | Almond |
| 2005/0096622 A1 | 5/2005 | Almond |
| 2006/0247592 A1 | 11/2006 | Schmidt-Forst et al. |
| 2007/0112320 A1 | 5/2007 | Pauley et al. |
| 2008/0108861 A1 | 5/2008 | Harris et al. |
| 2009/0095304 A1 | 4/2009 | Richardson et al. |
| 2011/0152605 A1 | 6/2011 | Hull, Jr. et al. |
| 2012/0136199 A1 | 5/2012 | Hou et al. |
| 2012/0165601 A1 | 6/2012 | Ellefson et al. |
| 2012/0215135 A1 | 8/2012 | Galliano et al. |

* cited by examiner

INTRAVAGINAL DEVICE WITHDRAWAL ASSEMBLY

FIELD OF INVENTION

This application relates to a withdrawal assembly for an intravaginal device.

BACKGROUND OF THE INVENTION

Intravaginal devices are inserted inside the vaginal canal for many different purposes from absorbing menses to managing urinary incontinence. Such devices are designed for arrangement in the vagina and must be removed after a prescribed duration of use. A withdrawal assembly can be joined to the intravaginal device to ease with removal of the device. The withdrawal assembly should remain attached to the device. As such, there remains a need to join the withdrawal assembly in a manner that secures the withdrawal assembly and allows for ease of removal.

SUMMARY OF THE INVENTION

An intravaginal device having a withdrawal assembly and an aperture. The withdrawal assembly comprises a withdrawal member and an obstruction. The obstruction of the withdrawal assembly at least partially blocks the intravaginal device aperture.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

The present invention is directed to a withdrawal assembly for an intravaginal device having an aperture. The withdrawal assembly has a withdrawal member and an obstruction. The obstruction can at least partially block the aperture in the intravaginal device thereby joining the withdrawal member to the intravaginal device.

The withdrawal assembly has a withdrawal member for ease of removal after use of the intravaginal device. The withdrawal member can be joined to an obstruction. The obstruction can have an insertion mode and a functional mode. The insertion mode can be a non-expanded mode. The functional mode can be an expanded mode. The obstruction can be compressible. The obstruction can be flexible. The obstruction can be contained inside the intravaginal device. The obstruction can be part of the outer profile of the intravaginal device. The obstruction can be surrounded by the intravaginal device.

The obstruction can be contained inside the intravaginal device by any aperture opening to the hollow interior of a device. The obstruction can be contained inside the intravaginal device by the shape of the intravaginal device. For example, if the intravaginal device is a hollow pessary, the obstruction can be contained inside the device by a waist of the pessary device itself. The obstruction can also be contained inside the device by one or more internal protuberances within a hollow interior of an intravaginal device.

As used herein, "applicator" refers to a device or implement that facilitates the insertion of the intravaginal device into an external orifice of a mammal. Exemplary applicators include telescoping, tube and plunger, and compact applicators.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to, encompassed by, or enrobed by the second element; and configurations in which first element is integral with second element, i.e., first element is essentially part of the second element.

The term "compressed," as used herein, refers to pressing or squeezing together or otherwise manipulating the size, shape, and/or volume.

As used herein, "fluid wicking" refers to the ability of a material to carry fluid or moisture by capillary action. The fluid wicking capacity of a medium can be measured by grams of fluid drawn per gram of tampon weight over a fixed period of time.

As used herein, the term "intravaginal device" refers to a device inserted inside the vaginal canal. Intravaginal devices include but are not limited to: tampons, pessary devices, devices for drug delivery, intrauterine devices, and/or birth control devices.

As used herein, the term "non-expandable" refers to devices that do not expand prior to or during use, such as, for example, devices that do not increase in size or volume prior to or during use. For example, non-expandable devices have a diameter and/or volume that do not increase. In contrast, "expandable", as used herein, refers to devices that do expand prior to or during use, such as, for example, devices that do increase in size or volume prior to or during use, such as, for example, devices that increase in diameter and/or length, absorb fluid into a fibrous or absorbent gelling material structure, or otherwise change from a first size or volume to a second size or volume, such as, for example, by inflation, absorption, mechanically, or by other means. Insubstantial changes to a non-expandable device as a result of any thermal expansion that could occur at body temperatures are not considered expansions.

A "pessary device," or more particularly an "incontinence pessary device," as used herein, refers to devices specifically designed, configured, and/or adapted for placement into a vagina in order to reduce the occurrence and/or severity of female urinary incontinence. A "pessary device" can include any type of substantially non-absorbent structure for the purpose of reducing urine leakage and/or supporting a prolapsed uterus and/or bladder. A pessary device does not include a menstrual tampon.

As used herein, the term "protuberances" refers to something that bulges out or that projects from its surroundings.

The terms "pledget" and "tampon pledget," as used herein, refer to a construction of absorbent material prior to the compression of such construction into a tampon as described below. Tampon pledgets are sometimes referred to as tampon "blanks" or a "softwind," and the term "pledget" is intended to include such terms as well.

The term "tampon," as used herein, refers to any type of absorbent structure that is inserted into the vaginal cavity or other body cavities for the absorption of fluid therefrom. Typically, tampons are constructed from a generally elongated absorbent member that has been compressed and/or formed into a vaginally insertable shape.

As used herein, the term "vaginal canal" refers to the internal genitalia of the human female in the pudendal region of the body. The terms "vaginal canal" or "within the vagina," as used herein, are intended to refer to the space located between the introitus of the vagina (sometimes referred to as the sphincter of the vagina) and the cervix.

As used herein, "cm" is centimeter, "mm" is millimeter, "g" is gram, "gsm" is grams per meter squared, "dpf" is denier per fiber, "g/g" is gram of fluid per gram of sample, "wt" is weight, "psi" is pound per square inch.

Withdrawal Assembly

Figure 1A:
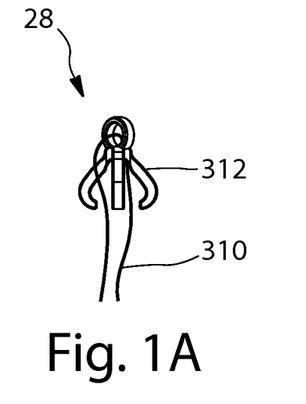
FIGS. 1A-C are examples of a withdrawal assembly.
Figure 1B:
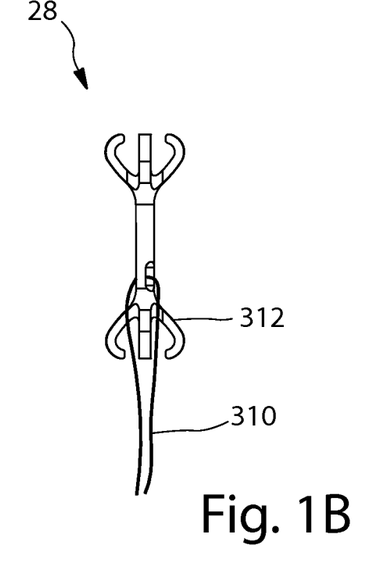
Figure 1C:
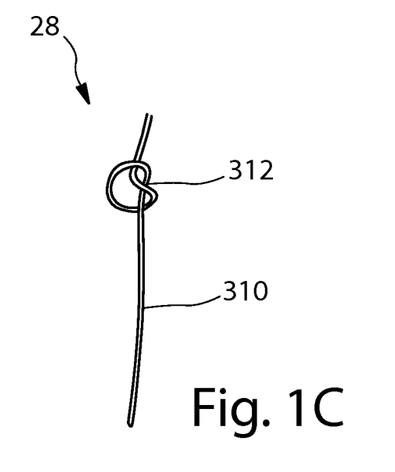
Figure 2A:
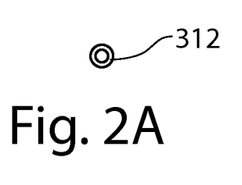
FIGS. 2A-L are examples of obstructions.
Figure 2B:
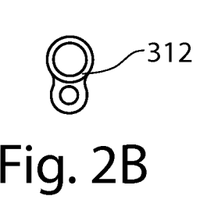
Figure 2C:
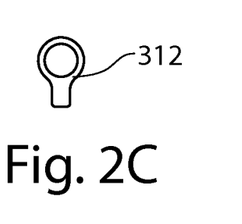
Figure 2D:
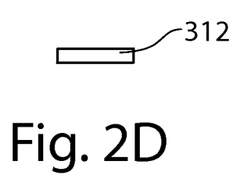
Figure 2E:
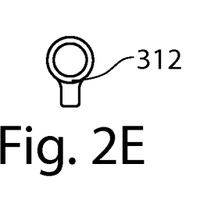
Figure 2F:
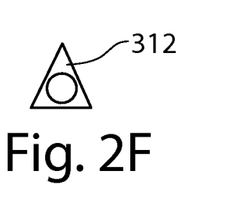
Figure 2G:
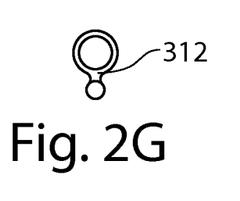
Figure 2H:
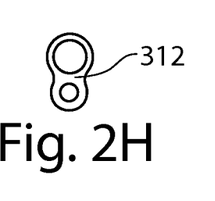
Figure 2I:
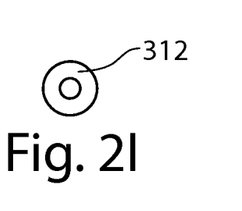
Figure 2J:
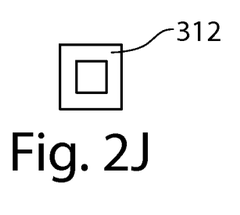
Figure 2K:
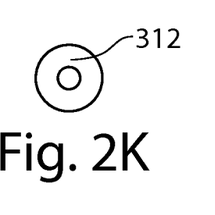
Figure 2L:
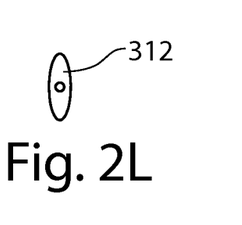

FIGS. 1A-C are examples of a withdrawal assembly 28. The withdrawal assembly 28 has a withdrawal member 310 and an obstruction 312.

The withdrawal member 310 can comprise any suitable material including, for example: cotton, cellulose, rayon, polyolefins such as, for example, polyethylene or polypropylene, nylon, silk, polytetrafluoroethylene, wax, or any other suitable materials.

The withdrawal member 310 can be non-absorbent. As used herein, the term "non-absorbent" refers to a structure that does not retain a significant portion of deposited fluid in its structure. The withdrawal member 310 can be inherently non-wettable or hydrophobic, or can be treated to provide such properties. For example, a coating of wax can be applied to the withdrawal member 310 to decrease or eliminate its absorbency. The withdrawal member 310 need not necessarily be non-fluid wicking, even if a non-absorbent withdrawal member 310 is desired.

The withdrawal member 310 can be any suitable length, such as, for example, a length from about 100 mm to about 500 mm, about 200 mm to about 400 mm, such as, for example, about 150 mm, about 175 mm, about 200 mm, about 225 mm, about 250 mm, about 275 mm, about 300 mm, about 325 mm, about 350 mm, about 375 mm, about 400 mm, about 425 mm, about 450 mm, about 475 mm, or about 500 mm.

The withdrawal member 310 can be formed by any suitable formation method and in any suitable configuration, such as, for example, one or more cords, strings, finger covers, ribbons, an extension of a material of the intravaginal device, or combinations thereof.

The withdrawal assembly 28 can have an obstruction 312. The withdrawal member 310 can be joined to the obstruction 312. The withdrawal member 310 can go through the obstruction 312. The obstruction 312 can be molded around the withdrawal member 310. The obstruction 312 can be part of the withdrawal member 310. The withdrawal member 310 can be molded around the obstruction 312. The withdrawal member 310 can be joined to the obstruction 312 such that, placing forces on the withdrawal member 310 can cause the obstruction 312 to expand.

The obstruction 312 can be made of any suitable material. The obstruction 312 can be formed from polymeric materials, such as, for example, polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, or metallic materials. The obstruction 312 can be formed from part of the withdrawal member 310.

As shown in FIG. 2A-L, the obstruction 312 can be any suitable shape. The obstruction 312 can be, for example, a disk, a cone, a star, a jack, a ball, a dumb bell, a drum, or a cross. The obstruction 312 can comprise of one or more interconnected parts. The obstruction 312 can be a hook or multiple hooks.

The obstruction 312 can have an insertion mode and a functional mode. The insertion mode can be the obstruction 312 in a non-expanded mode. The obstruction 312 can be compressible. The obstruction 312 can be flexible. The functional mode can be a volumetrically expanded mode. The obstruction 312 can transition between the insertion mode and the functional mode by hinge points in the obstruction 312 allowing the obstruction 312 to change volumetrically.

The withdrawal assembly 28 can be used with any intravaginal device having an aperture in the intravaginal device. The obstruction 312 can be located on one end of the aperture. The withdrawal member 310 can cross through the aperture. The withdrawal assembly 28 can be used with intravaginal devices such as, for example, tampons and pessaries.

Tampon

Figure 3:
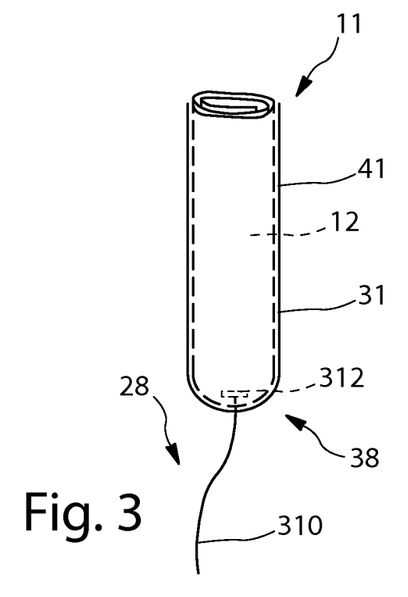
FIG. 3 exemplifies a finished tampon.

FIG. 3 exemplifies a finished tampon 11 made from a pledget of the present invention. The present invention, however, is not limited to a structure having the particular configuration shown in the drawings. The tampon 11 can comprise a compressed absorbent member 12 comprising absorbent material 31, and an overwrap 41 that substantially covers the absorbent material 31 of the compressed absorbent member 12. The tampon can be rolled construction or flat pad construction. The tampon 11 can include a withdrawal assembly 28 having an obstruction 312 and a withdrawal member 310 extending beyond the tampon withdrawal end 38. The obstruction 312 is not sown to the absorbent material 31. The obstruction 312 can be held by friction within the tampon 11. The obstruction 312 can be contained within the compressed absorbent member 12 by the overwrap 41.

Absorbent Material

Figure 4:
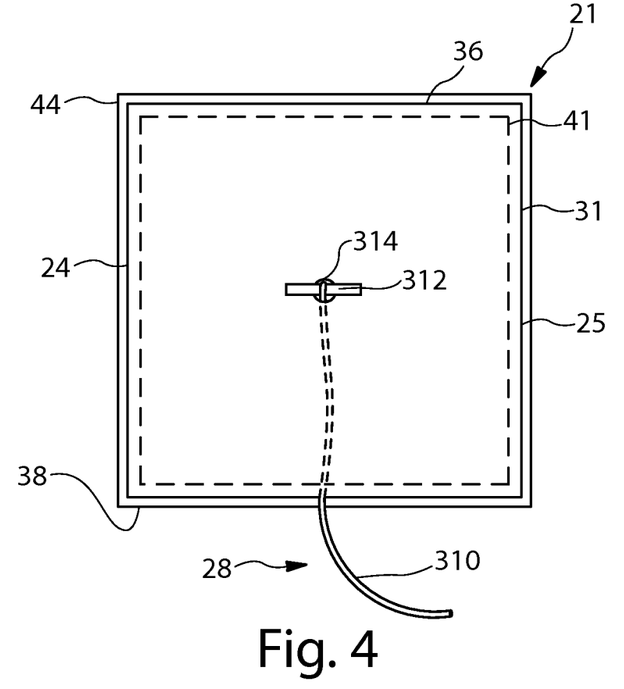
FIG. 4 exemplifies a tampon pledget in a flat-out, uncompressed state.

FIG. 4 exemplifies a tampon pledget 21 in a flat-out, uncompressed state. The absorbent material 31 of the present invention forms a tampon pledget 21. The tampon pledget 21 comprises an insertion end 36, a withdrawal end 38, a first longitudinal edge 24, and a second longitudinal edge 25. A withdrawal assembly 28 having an obstruction 312 and a withdrawal member 310 that crosses through an aperture 314 in the absorbent material 31. Compression of a tampon pledget 21 can form a compressed absorbent member 12 (as shown in FIG. 3). A compressed absorbent member 12 in combination with a withdrawal assembly 28 can form a tampon 11 (as shown in FIG. 3). The pledget 21 can have an overwrap 41 and an additional optional second overwrap 44.

The overwrap may comprise a fibrous liquid permeable non-woven material comprising a blend of synthetic and natural fibers. The synthetic fibers may include, but are not limited to, fibers such as polyester, polyolefin, nylon, polypropylene, polyethylene, polyacrylic, cellulose acetate, or bicomponent fibers. Natural fibers may include, but are not limited to, those commonly known to be non-synthetic and of natural origin such as cotton and/or rayon. In general, the natural fibers may provide ready absorption and fluid wicking strength. The ratio of synthetic fibers to natural fibers may fall in the range of from about 90:10 to about 30:70. Alternatively, the ratio of synthetic fibers to natural fibers may fall in the range of from about 70:30 to about 40:60. The synthetic fibers may have hydrophobic and/or hydrophilic surfaces. The synthetic fibers may be inherently hydrophilic, or may preferably be treated to provide such properties.

The tampon pledget 21 can be any suitable shape, size, material, or construction for compression or formation into a tampon 11 having a vaginally insertable shape. The absorbent material 31 can be generally square or rectangular or take on other shapes such as trapezoidal, triangular, hemispherical, chevron, or hourglass shapes.

Figure 5:
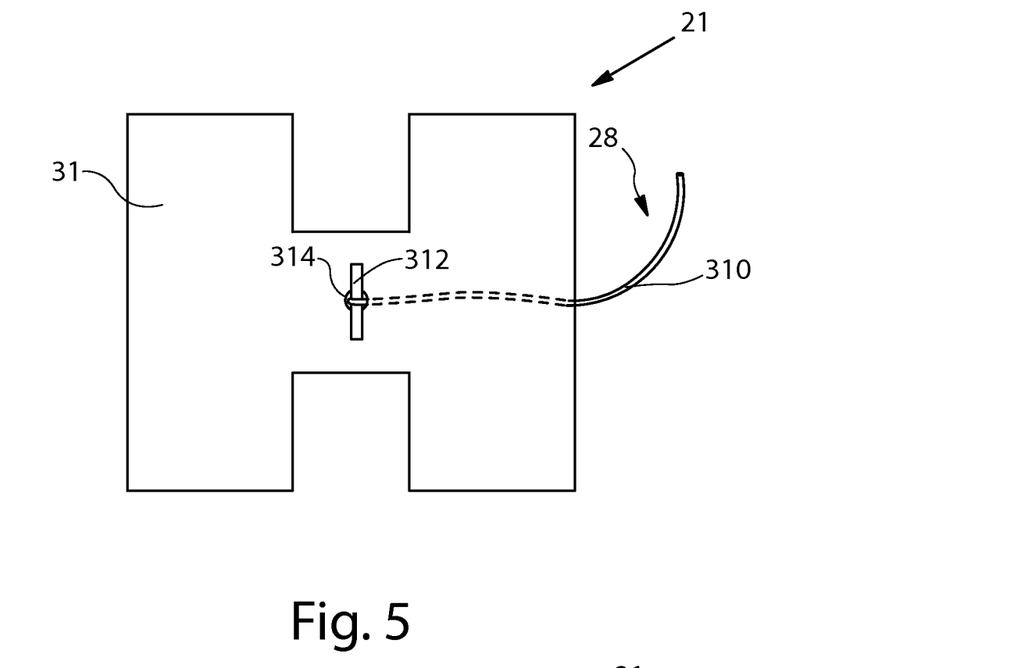
FIG. 5 exemplifies a tampon pledget in a flat-out, uncompressed state.
Figure 6:
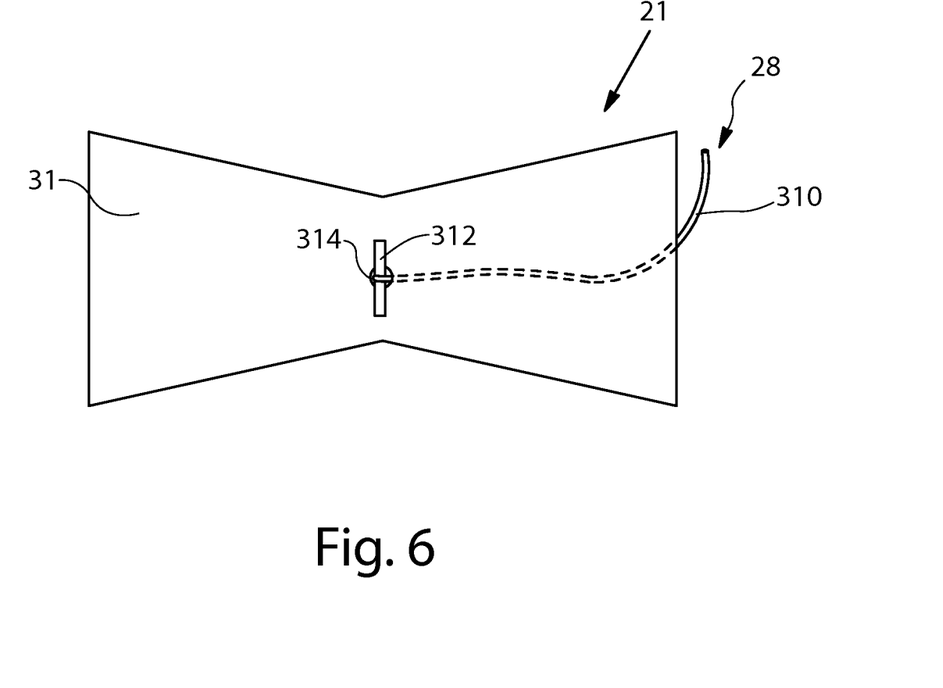
FIG. 6 exemplifies a tampon pledget in a flat-out, uncompressed state.

The tampon pledget 21 can be a batt of absorbent material 31 in any suitable shape. For example, the pledget 21 can be generally "H" shaped, such as shown in FIG. 5. A "bow tie" shaped tampon pledget 21, such as is shown in FIG. 6, is also suitable. The tampon pledget 21 can be a generally "chevron shaped" pad of absorbent material 31. While a chevron shaped pledget 21 can be suitable, the edges of the chevron can be somewhat "rounded off" in order to facilitate high speed manufacturing operations. Other shapes such as trapezoidal, triangular, semi-circular, and rectangular shaped are also acceptable. As show in FIGS. 5 and 6, the pledget 21 has an aperture 314 and a withdrawal assembly 28. The withdrawal assembly 28 has an obstruction 312 and a withdrawal member 310. The obstruction 312 at least partially blocks the aperture 314. The withdrawal member 310 crosses through the aperture 314.

As an alternative to the shapes of pledgets 21 described above, a tampon pledget 21 of the present invention can have a uniform shape such as a rectangular shape but can vary in absorbent material 31 thickness along the axial extent of the pledget 21.

The tampon pledget 21 can be constructed from a wide variety of liquid-absorbing materials commonly used in absorbent articles such as rayon (including tri-lobal and conventional rayon fibers), cotton, or comminuted wood pulp which is generally referred to as airfelt. Examples of other suitable absorbent materials include, but are not limited to, creped cellulose wadding; meltblown polymers including coform; chemically stiffened, modified, or cross-linked cellulosic fibers; synthetic fibers such as crimped polyester fibers; peat moss; foam; tissue including tissue wraps and tissue laminates; or any equivalent material or combinations of materials, or mixtures thereof.

Typical absorbent materials can comprise cotton, rayon folded tissues, woven materials, non-woven webs, synthetic and/or natural fibers or sheeting. The tampon 11 and any component thereof can comprise a single material or a combination of materials. Additionally, superabsorbent materials, such as superabsorbent polymers or absorbent gelling and open-celled foam materials can be incorporated into the tampon 11.

The absorbent material 31 and resulting compressed absorbent member 12 (shown in FIG. 3) can comprise rayon, cotton, or combinations of both materials. These materials have a proven record of suitability for use in the human body. The rayon used in the absorbent material 31 can be any suitable type typically used in disposable absorbent articles intended for in vivo use. Such acceptable types of rayon include GALAXY Rayon (a tri-lobed rayon structure) available as 6140 Rayon from Acordis Fibers Ltd., of Hollywall, England. SARILLE L rayon (a round fiber rayon), also available from Acordis Fibers Ltd. is also suitable. Any suitable cotton material can be used in the absorbent material 31. Suitable cotton materials include, long fiber cotton, short fiber cotton, cotton linters, T-fiber cotton, card strips, and comber cotton. The cotton can be scoured and bleached cotton absorbent with a glycerin finish, or other suitable finish.

The absorbent material 31 can be a laminar structure comprised of integral or discrete layers. If the compressed absorbent member 12 of the present invention is layered, the layers can comprise different materials. For example, the outer layers can comprise primarily rayon, while the intermediate layer or layers can comprise primarily cotton. Optionally, the entire compressed absorbent member 12 can comprise a uniform or non-uniform blend of materials throughout. The absorbent material can comprise 100% rayon fibers or 100% cotton fibers. The absorbent material can comprise a combination of rayon and cotton fibers in any suitable combination. The absorbent material can comprise greater than about 25%, 30%, or 40% rayon fibers and the balance of the absorbent material comprising cotton fibers. The absorbent material of the present invention can comprise greater than about 50% rayon fibers with cotton fibers comprising the balance of the absorbent material. The absorbent material can comprise greater than about 60, 70, 75, 80, or 90% rayon fibers and the balance of the absorbent material comprising cotton fibers. Each of the layers can comprise essentially 100% of the same material, such as outer layers of 100% rayon and an intermediate layer of 100% cotton. A Super Plus absorbency tampon of the present invention can be made from a pledget comprising about 100% rayon fibers. A Super absorbency or Regular absorbency tampon of the present invention can be made from a pledget comprising about 25% cotton and about 75% rayon fibers. A Junior absorbency tampon can be made from a pledget comprising about 50% cotton and about 50% rayon fibers.

A typical size for absorbent material 31 prior to compression can be from about 30 or 40 mm to about 60, 70, 80, 90, or 100 mm in length and from about 40 or 50 mm to about 70, 75, 80, 85, or 90 mm in width. The typical range for the overall basis weight can be from about 150, 200, or 250 gsm to about 600, 800, 1000, or 1100 gsm.

As shown in FIGS. 4 to 6, one or more layers of the tampon pledget 21 have an aperture 314. The aperture 314 may be any suitable size such that the one dimension of the obstruction 312 is larger than one dimension of the aperture 314. The withdrawal member 310 crosses through the aperture 314.

Optional Tampon Components

The tampon 11 can include an additional overwrap 44 as shown in FIG. 4. This additional overwrap can substantially cover the overwrap 41 that substantially covers the exterior surface of the compressed absorbent member 12 of the tampon 11. This additional overwrap can be added prior to or subsequent to compression of the absorbent material to form a compressed absorbent member.

Figure 11:
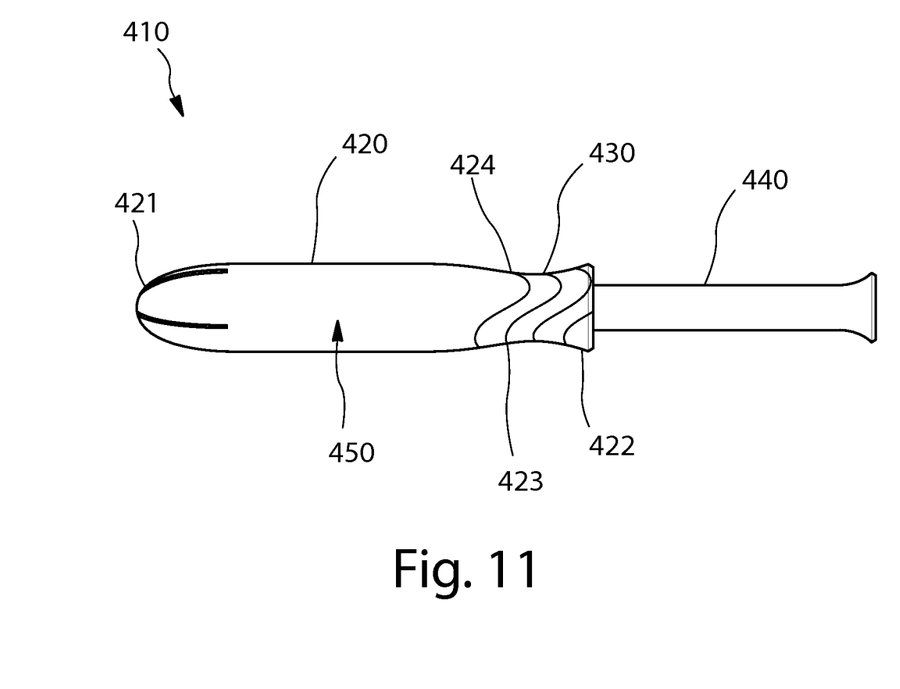
FIG. 11 is a side view of an applicator.

The tampon 11 can be inserted digitally or through the use of an applicator as shown in FIG. 11. Any of the currently available tampon applicators can also be used for insertion of the tampon 11. Such applicators of typically a "tube and plunger" type arrangement can be plastic, paper, or other suitable material. Additionally, a "compact" type applicator is also suitable.

Pessary Device

Figure 7A:
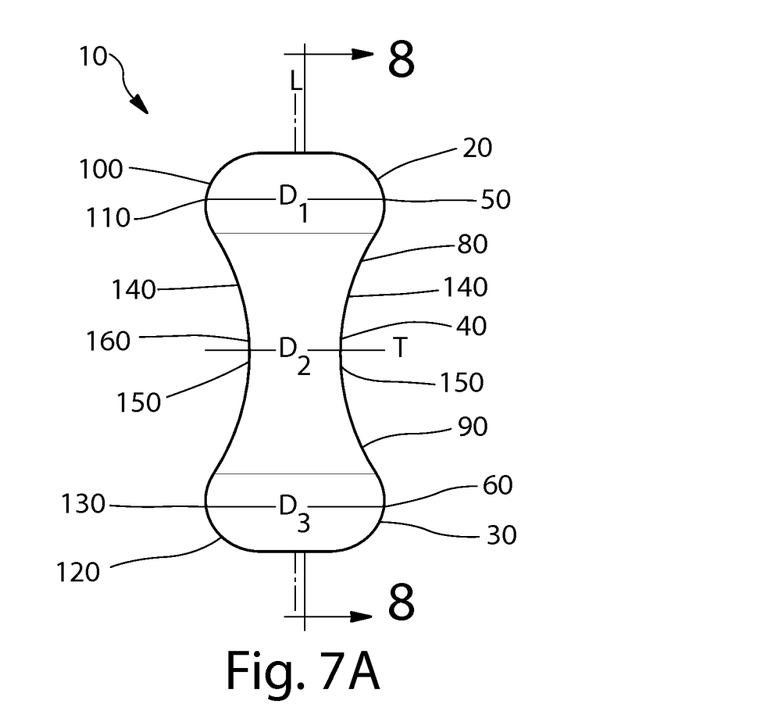
FIG. 7A is a side view of a pessary device.
Figure 7B:
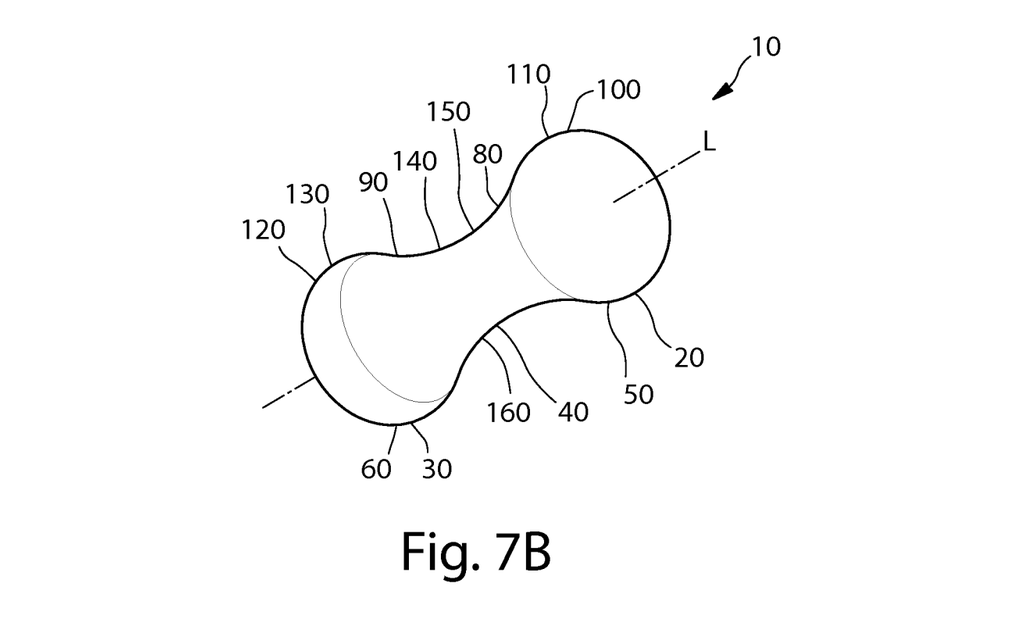
FIG. 7B is a perspective view of the pessary device of FIG. 7A.

An exemplary pessary device 10 is shown in FIGS. 7A and 7B. The pessary device 10 includes an upper portion 20, a lower portion 30, a middle portion 40, a pressure region 50 of the upper portion 20, a pressure region 60 of the lower portion 30, a maximum diameter $D_1$, a minimum diameter $D_2$, a slope 80 extending from the upper portion 20 to the middle portion 40, a slope 90 from the middle portion 40 to the lower portion 30, a longitudinal axis (L) and a transverse axis (T). As shown in FIGS. 7A and 7B, the pessary device 10 can have a top 100 that includes a convex portion 110, a base 120 that includes a convex portion 130, and sides 140 that include concave portions 150. The pessary device can be symmetric about the longitudinal axis, including for example, wherein the base is circular and symmetric about the longitudinal axis. The pessary device can include a third diameter $D_3$ that is greater than minimum diameter $D_2$, and convex portion 110 can be aligned with maximum diameter $D_1$ to provide pressure region 50, and convex portion 130 can be aligned with maximum diameter $D_3$ to provide pressure region 60. In addition, concave portion 150 can be aligned with minimum diameter $D_2$ to form flexile region 160.

Figure 8:
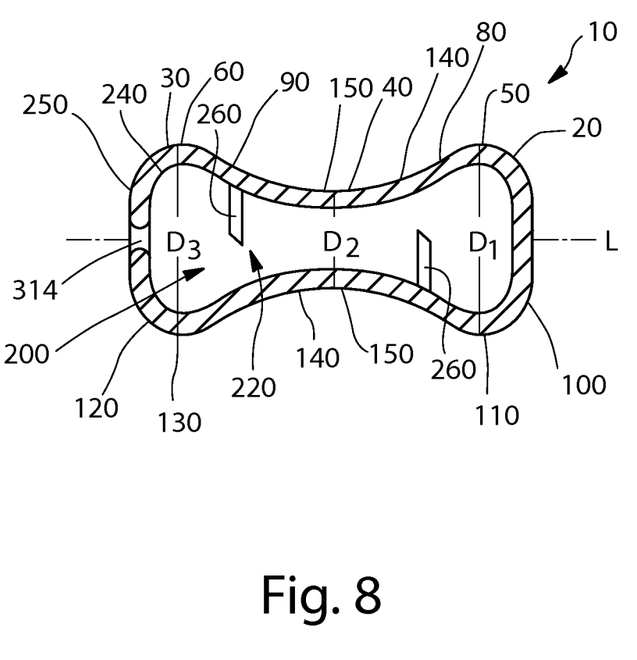
FIG. 8 is a cross section view of a pessary device as taken through line 8-8 in FIG. 7A.

FIG. 8 shows a cross section of the pessary device 10 as taken through line 8-8 in FIG. 7A. The pessary device 10 includes an upper portion 20, a lower portion 30, a middle portion 40, a pressure region 50 of the upper portion 20, a pressure region 60 of the lower portion 30, a maximum diameter $D_1$, a minimum diameter $D_2$, a slope 80 extending from the upper portion 20 to the middle portion 40, a slope 90 from the middle portion 40 to the lower portion 30, and a longitudinal axis (L). As shown in FIG. 8, the pessary device 10 can have a top 100 that includes a convex portion 110, a base 120 that includes a convex portion 130, and sides 140 that include concave portions 150. As shown in FIG. 8, the pessary device 10 can have an interior 200 that is hollow. The pessary device has inner walls 240 that define interior 200 and hollow region 220. The hollow region 220 can have one or more protuberances 260 extending from the inner wall 240. In addition, the inner walls 240 can have the same or a similar profile as the outer walls 250.

Figure 9A:
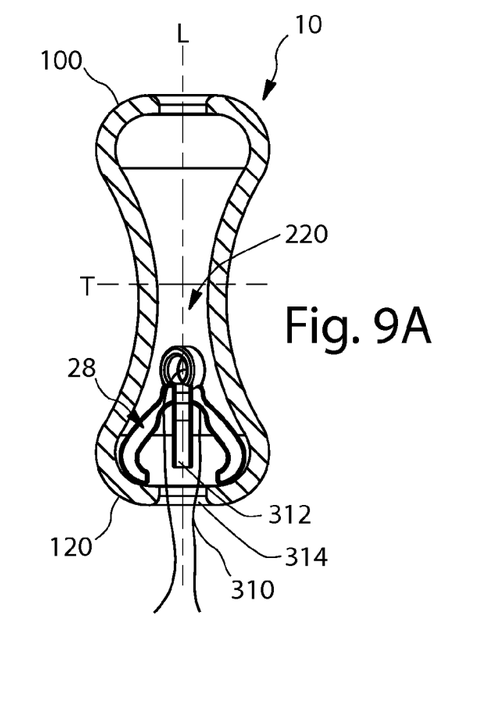
FIGS. 9A-D are cross-section views of a pessary device with a withdrawal assembly.
Figure 9B:
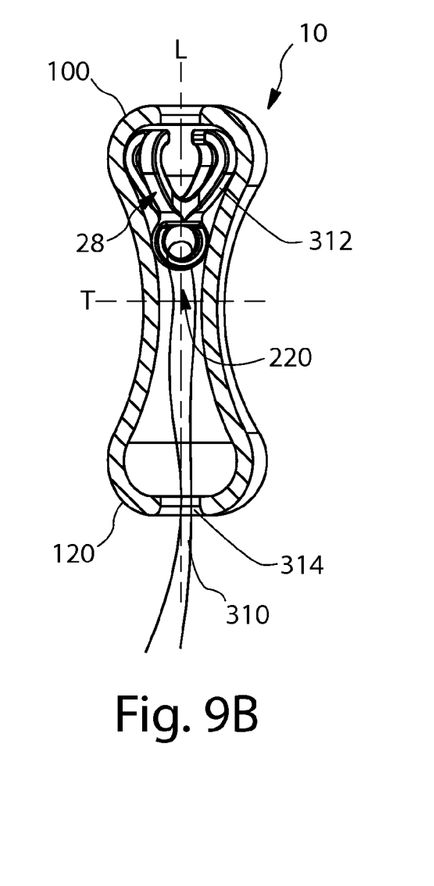
Figure 9C:
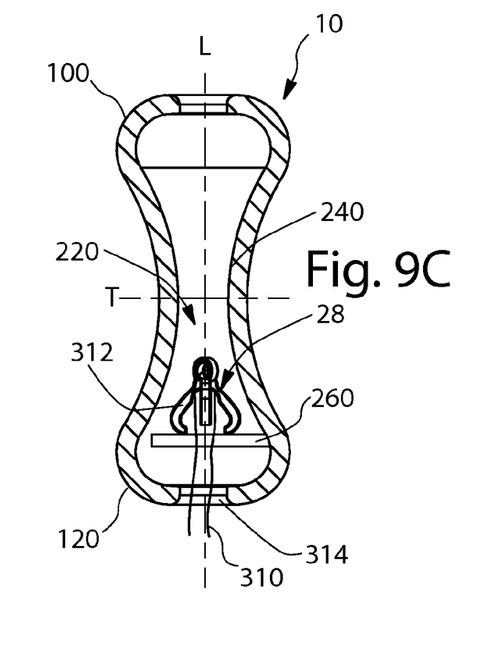

FIGS. 9A-D show cross sections of multiple pessary devices 10 taken along line 8-8 of FIG. 7A having a withdrawal assembly 28. The pessary devices 10 can have an interior 200 that is hollow. In addition, as shown in FIGS. 9A-D, the pessary device 10 can have an aperture 314 on one or more of top 100 and/or on base 120. As shown in FIGS. 9A-C, the pessary device 10 can have a longitudinal axis L and a transverse axis T.

As shown in FIGS. 9A-D, The intravaginal device can comprise an aperture 314. The aperture 314 can be through any surface of the intravaginal device. The aperture 314 can be between the outside of a hollow intravaginal device to the hollow interior. The aperture 314 can be between an inner layer and an outer layer of an intravaginal device. The obstruction 312 can have one dimension greater than one dimension of the aperture 314. The obstruction 312 can have dimensions, such as, for example, an outer length, an outer height, and an outer width. One of the obstruction 312 dimensions can be greater than the largest dimension of the aperture 314.

As shown in FIGS. 9A and 9B, a portion of the withdrawal assembly 28 can be contained by the intravaginal device. The obstruction 312 can be contained inside the pessary device 10. The obstruction 312 can be contained inside the pessary device 10 by any opening to the hollow region 220 of the pessary device 10. The obstruction 312 can be contained inside the intravaginal device by the shape of the device. For example, the obstruction 312 can be contained inside the device by a waist of the intravaginal device itself. The obstruction 312 can move freely within the portion of the hollow region 220 containing the obstruction 312. The obstruction 312 can at least partially blocks the aperture 314. The withdrawal member 310 crosses through the aperture 314.

As shown in FIGS. 9B and 9A, the obstruction 312 can have one dimension greater than one dimension of the aperture 314. The obstruction 312 can have dimensions, such as, for example, an outer length, an outer height, and an outer width. One of the obstruction 312 dimensions can be greater than the smallest dimension of a transverse axis area running along a longitudinal axis (L) of a hollow intravaginal device.

As shown in FIG. 9C, the hollow region 220 can contain one or more protuberances 260 that can be integral or non-integral to the inner wall 240. The protuberances 260 can cross the longitudinal axis of the pessary device. The protuberances 260 can contact at the longitudinal axis or between the longitudinal axis and the inner wall. The protuberances 260 can interlock with each other. The obstruction 312 can be contained inside the intravaginal device by internal protuberances 260 within the hollow interior of the device. The obstruction 312 can move freely inside the hollow region 220 of the device. The withdrawal member 310 crosses through the aperture 314.

Figure 9D:
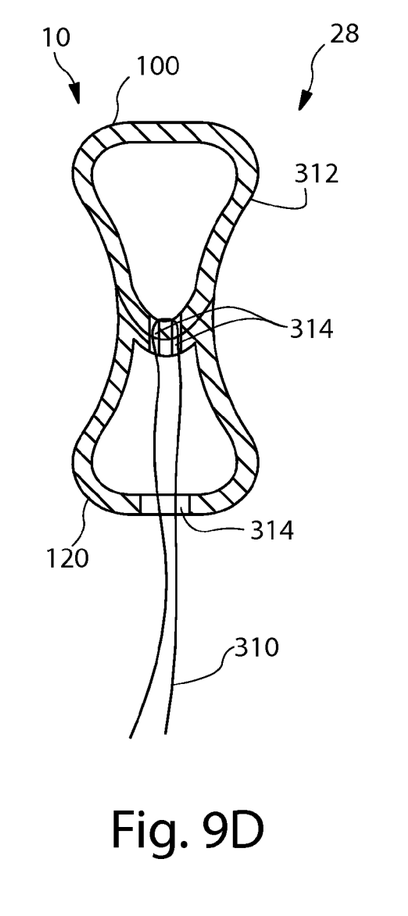

As shown in FIG. 9D, the withdrawal assembly 28 can be joined to the intravaginal device by friction. A portion of the withdrawal assembly 28 can be part of the outer profile of the pessary device 10. The withdrawal member 310 crosses through the aperture 314.

Figure 10:
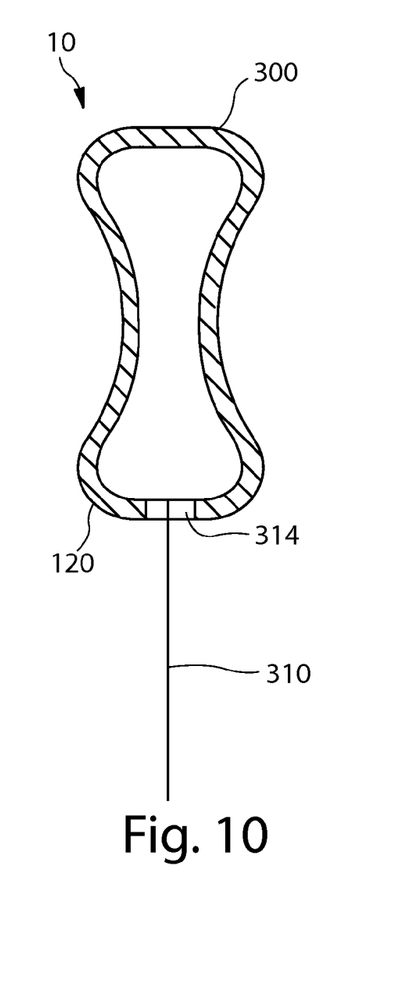
FIG. 10 is a side view of a pessary device.

The pessary device 10 can include an overwrap 300, such as, for example, as shown in FIG. 10.

The pessary device can be inserted in any suitable manner, such as, for example, using an applicator. FIG. 11 shows an applicator 410 that includes an insertion member 420 and a plunger 440. The insertion member 420 has an insertion end 421 and a withdrawal end 422 opposite the insertion end 421. The insertion member 420 also can include a barrel region 450 adapted to contain a pessary device, and a grip region 430 that can be an indentation region 424 provided opposite the insertion end 421, such as, e.g., proximal to the withdrawal end 422. The grip region 430 can include one or more grip elements 423.

The pessary device can be non-expandable. A portion or region of the pessary device can flex or be deformed, such as, for example, in the region having the minimum diameter, but the pessary device does not expand and returns to the original configuration after deformation. As such, the pessary device does not include any mechanical or other means that requires the user to change the size or shape of the pessary device during use, such as, for example, before or after insertion or prior to withdrawal. This provides for a pessary device that has a size upon withdrawal that is the same as the size during use, which can provide for improved comfort during use and withdrawal.

The pessary device can have a pressure region that has the maximum diameter of the pessary, such as, for example, at the base or at the top, that extends between the anterior vaginal wall and the posterior vaginal wall of a consumer to provide pressure on the urethra through the vaginal wall. In addition, the pessary device can have a second pressure region having an increased diameter as compared to the minimum diameter that can provide pressure on the urethra through the vaginal wall at a point apart from the first pressure region. The first pressure region and the second pressure region can be separated by any suitable distance, such as, for example, by at least about 5 mm, at least about 10 mm, at least about 15 mm, at least about 20 mm, at least about 25 mm, at least about 30 mm, at least about 35 mm, at least about 40 mm, at least about 45 mm, or at least about 50 mm.

The pessary device can have any suitable number of pressure regions, including for example, two pressure regions, such as, for example, four or fewer pressure regions, three or fewer pressure regions, two or fewer pressure regions, one pressure region, or any other suitable number of pressure regions.

The pressure region or regions can be any suitable shape, such as, for example, a convex shape that provides pressure to the vaginal wall, including, for example, a lobe. The pressure region or regions can have a substantially circular cross-section. The pessary device also can include a minimum diameter region that is a flexile region that can provide flexibility to the pessary device, such as, for example, by allowing bending or movement at the flexile region. The flexile region can be any suitable shape, such as, for example, concave, indented, or the like, and can have any suitable cross-section, such as, for example, a substantially circular cross-section. The pessary device can include a flexile region provided between two pressure regions.

The pessary device can provide resistance to force when placed inside a woman's vagina. For example, when the pessary device is inserted into the vagina, increases in abdominal pressure can act as a force on the pessary device through the vaginal wall. When the pessary device is disposed in the vagina lengthwise, that is, with the top of the pessary device positioned toward the cervix, the bottom of the pessary device positioned toward the introitus, and the length of the pessary device generally aligned with the length of the vagina, increases in abdominal pressure can act on the side of the pessary device, perpendicular to the length of the pessary device. Of course, increases in abdominal pressure can act on other regions of the pessary device, in addition or alternatively to acting on the side of the pessary device, including for example, when the pessary device is inserted into the vagina in an orientation other than lengthwise.

Despite its small size, the pessary device can provide a resistance to force of greater than about 10 psi, greater than about 15 psi, greater than about 20 psi, or greater than about 25 psi under about 2 newtons of force. For example, the pessary device can provide a resistance to force of greater than about 20 psi under about 2 newtons of force and greater than about 25 psi under about 3 newtons of force. The pessary device also can resist compression under pressure. For example, the pessary device can compress less than about 20% under about 2 newtons of force, less than about 15% under about 2 newtons of force, less than about 14% under about 2 newtons of force, less than about 13% under about 2 newtons of force, less than about 12% under about 2 newtons of force, less than about 11% under about 2 newtons of force, less than about 10% under about 2 newtons of force, less than about 9% under about 2 newtons of force, less than about 8% under about 2 newtons of force, less than about 7% under about 2 newtons of force, less than about 6% under about 2 newtons of force, less than about 5% under about 2 newtons of force, less than about 4% under about 2 newtons of force, less than about 3% under about 2 newtons of force, less than about 2% under about 2 newtons of force, or less than about 1% under about 2 newtons of force. For example, the pessary device can compress less than about 20% under about 2 newtons of force, less than about 15% under about 2 newtons of force, less than about 14% under about 2 newtons of force, less than about 13% under about 2 newtons of force, less than about 12% under about 2 newtons of force, less than about 11% under about 2 newtons of force, less than about 10% under about 2 newtons of force, less than about 9% under about 2 newtons of force, less than about 8% under about 2 newtons of force, less than about 7% under about 2 newtons of force, less than about 6% under about 2 newtons of force, less than about 5% under about 2 newtons of force, less than about 4% under about 2 newtons of force, less than about 3% under about 2 newtons of force, less than about 2% under about 2 newtons of force, or less than about 1% under about 2 newtons of force.

The pessary devices can provide a varied resistance to force along the longitudinal axis of the pessary device. For example, the pessary device can provide a resistance to force that is greater at the maximum diameter regions and smaller at the minimum diameter regions. In addition, the pessary device can compress differently along the longitudinal axis at different regions. For example, when force is applied to the side of the pessary, the minimum diameter region can compress at least about 5% more than the maximum diameter region under the same amount of pressure (for example, under about 200 g/m² of force), at least about 10% more than the maximum diameter region under the same amount of pressure, at least about 15% more than the maximum diameter region under the same amount of pressure, at least about 20% more than the maximum diameter region under the same amount of pressure, or at least 25% more than the maximum diameter region under the same amount of pressure. Any suitable amount of force can be applied, such as, for example, from about 200 g/m² of force to about 1500 g/m² of force, from about 200 g/m² of force to about 1400 g/m² of force, from about 300 g/m² of force to about 1200 g/m² of force, or from about 400 g/m² of force to about 800 g/m² of force.

The amount of resistance to force and the amount of compression under force provided by the pessary device as a whole or provided by the different regions of the pessary device can be measured in any suitable manner. For example, one suitable method employs a Universal Constant Rate Elongation/Tensile Tester with computer interface (MTS, Eden Prairie, Minn.). The method measures the force required to compress the pessary device resting on its side at 0.8 mm at a rate of 20 mm per min. For this method, the load probe tip is 5 mm in diameter and the tip is semi-spherical in shape. In addition, the resting fixture is a cylindrical steel plate 152 mm in diameter and 13 mm thick. The pessary device is placed on the steel table and the crosshead moves at 20 mm/min. When a force of 2 grams is exhibited on the pessary device, the crosshead automatically zeroes out and moves an additional 0.8 mm. The probe cycles back, and data is acquired at a rate of 100 Hz. This method measures the peak force in grams versus the amount of compression in mm. For pessary devices having varying diameters or widths, such as, for example, pessary devices having a maximum diameter or width and a minimum diameter or width, resistance to force at the different regions can be measured using this method. For example, for a pessary device as shown in FIGS. 7A and 7B, resistance to force at the maximum diameter regions $D_1$ and $D_3$ can be measured using a steel plate that is larger in size than the pessary device as the resting fixture. Resistance to force at the minimum diameter region D2 can be measured using a single rod that contacts the minimum diameter region but not the maximum diameter regions.

Generally, the pressure region can be resistant such that the pressure region can provide pressure to the vaginal wall. The pressure region provides resistance under high stress pressures typical of the human vagina, such as, for example, by providing a maximum pressure to the urethra through the vaginal wall greater than about 5 psi, such as, for example, greater than about 10 psi, greater than about 15 psi, greater than about 20 psi, or greater than about 25 psi. In addition, the pressure region can provide a maximum urethral closure of greater than about 1.0 mm, such as, for example, greater than about 1.1 mm, greater than about 1.2 mm, greater than about 1.3 mm, greater than about 1.4 mm, such as, for example, greater than about 1.5 mm, greater than about 1.6 mm, greater than about 1.7 mm, greater than about 1.8 mm, or greater than about 1.9 mm. In addition, or alternatively, the pressure region can compress less than about 1 mm when measured under 0.5 psi when the force is applied from one side of the pressure region to the opposite side of the pressure region at the region of maximum diameter in the direction perpendicular to the longitudinal axis.

The flexile region, on the other hand, is more flexible than and provides less resistance than the pressure region. Addition of the flexile region can allow the pessary device to flex in the longitudinal direction as well at the lateral direction. For example, the pessary device can compress more than about 1 cm when measured under 0.5 psi when the force is applied from the top to the base along the longitudinal axis. In addition, or alternatively, the flexile region can provide a bending region that facilitates the pessary device bending from side to side.

The pessary device can be a unitary construction. For example, the pessary device can include a continuous outer shell that defines the entire exterior surface of the pessary device. The outer shell can be smooth or textured. The outer shell can be permeable to fluid, such as, for example, by the inclusion of holes, pores, or other suitable openings. Alternatively, the outer shell can be impermeable to fluid such that fluid cannot enter the device. In addition, the pessary device can include an opening in the top and/or base. The pessary device can include an opening in the top and/or base and the outer shell is not permeable to fluid such that fluid cannot enter the device except through the opening in the top and/or base.

The pessary device can be constructed from two or more pieces. The two or more pieces can snap fit together to form a continuous outer shell that defines the entire exterior surface of the pessary device. In addition, the pessary device can include an aperture in the top and/or base.

Suitable pessary devices can have a hollow interior. The pessary device can have an outer periphery defining a total area of the device and an inner periphery defining an open area of the device. The open area can be any suitable size, such as, for example, between about 5% to about 95% of the total area, such as, for example, from about 10% to about 90% of the total area, from about 15% to about 85% of the total area, or from about 20% to about 80% of the total area. In addition, the pessary device also can have a wall thickness that is suitable to maintain the pessary configuration. The wall thickness can be greater than about 1 mm, such as for example, about 2 mm, about 3 mm, about 4 mm, about 5 mm, or greater. The wall thickness can be constant or varied along the length of the pessary device and/or around the circumference of the pessary device.

The pessary device can have any suitable shape having a varied diameter along the longitudinal axis, such as, for example, a shape having a varied diameter that is symmetrical with respect to the longitudinal axis, such as, for example, a teardrop, an apple, a pear, an hourglass, a waisted cylinder, a figure-8 shape, a peanut shape, a heart-shape, a light bulb shape, a bottle shape, a vase shape, or any other suitable shape. In addition, the shape can have a varied diameter and can be symmetrical with respect to both the longitudinal and lateral axis, such as, for example, an hourglass, a waisted cylinder, a figure-8 shape, a peanut shape, or any other suitable shape. Alternatively, the pessary device can have an asymmetrical shape, such as, for example, a B-shape or a P-shape. The pessary device can be symmetrical at one region and asymmetrical at another region, such as, for example, where the pessary device has a symmetrical pressure region and an asymmetrical flexile region. Generally, the pessary device can have a varying diameter that can provide varying pressure along the user's urethra. For example, the pessary device can have a convex portion that can correspond to the pressure region. In addition, the pessary device can have a minimum diameter region that can be a concave region. The concave region can correspond to the flexile region.

The pessary device can be hourglass shaped. For example, as shown in FIG. 7, the pessary device can have upper and lower portions joined together by a waistline portion, with the upper and lower portions having diameters that are both greater than a diameter of the waistline portion such that the pessary device has a generally hourglass configuration. In this configuration, the upper portion of the pessary device can have a top and the lower portion of the pessary device can have a base, and the pessary device can have sloping upper and lower wall sections joining the top and the base with the waistline portion. In addition, the waistline portion can include the minimum diameter of the pessary device. The upper and lower portions can have generally coequal maximum diameters, or the upper and lower portions can have different maximum diameters, such as, for example, where the upper portion has a maximum diameter greater than the lower portion or where the lower portion has a maximum diameter greater than the upper portion.

Generally, the pessary device includes at least one maximum diameter and at least one minimum diameter, where the minimum diameter is smaller than the maximum diameter. The pessary device can include a first portion having a maximum diameter, a second portion having a maximum diameter, and a third portion that has a minimum diameter. The maximum diameter of the first portion and the maximum diameter of the second portion can be separated by a distance that is greater than about 10% of the length of the pessary device, such as, for example, by a distance greater than about 5 mm, greater than about 10 mm, greater than about 15 mm, greater than about 20 mm, greater than about 25 mm, greater than about 30 mm, greater than about 35 mm, greater than about 40 mm, greater than about 45 mm, or more. The pessary device can provide pressure at mid-urethra, the bladder neck, or both. In addition, the pessary device can provide higher pressure at the mid-urethra, the bladder neck, or both and provides lower pressure at the area between the mid-urethra and the bladder neck. For example, the pressure region can provide pressure at levels about 25% higher than the pressure provided by the flexile region, such as, for example, at levels about 30% higher, about 35% higher, about 40% higher, about 45% higher, about 50% higher, about 55% higher, about 60% higher, or more.

The pessary device can have a slope from the maximum diameter to the minimum diameter. Any suitable slope can be used, including for example, about 0.25 mm, about 0.5 mm, about 0.75 mm, about 1 mm, about 1.5 mm, about 2 mm, about 2.5 mm, about 3 mm, about 4 mm, about 5 mm, about 6 mm, about 7 mm, about 8 mm, or more, such as, for example, a slope from about 0.25 mm to about 5 mm, or a slope from about 0.5 mm to about 4 mm, or any other suitable range.

Suitable pessary devices are typically smaller in size than conventional pessary devices. For example, the pessary devices have a maximum diameter, a length, and/or a volume that is smaller or less than that of conventional pessary devices.

The pessary devices can have any suitable maximum diameter, such as, for example, a maximum diameter of less than 55 mm, such as, for example, less than 50 mm, less than 45 mm, less than 40 mm, less than 35 mm, less than 34 mm, less than 33 mm, less than 32 mm, less than 31 mm, less than 30 mm, less than 29 mm, less than 28 mm, less than 27 mm, less than 26 mm, less than 25 mm, less than 24 mm, less than 23 mm, less than 22 mm, less than 21 mm, less than 20 mm, less than 19 mm, less than 18 mm, less than 17 mm, less than 16 mm, less than 15 mm, less than 14 mm, less than 13 mm, less than 12 mm, less than 11 mm, or less than 10 mm, including, for example, a maximum diameter of from about 10 mm to about 35 mm, from about 10 mm to about 25 mm, from about 13 mm to about 25 mm, or from about 15 mm to about 22 mm. The maximum diameter or width is typically measured at the widest portion of the pessary device substantially perpendicular to the longitudinal axis.

The pessary devices can have any suitable minimum diameter that is smaller than the maximum diameter, including, for example, a minimum diameter from about 40% to about 95% of the maximum diameter, from about 40% to about 90% of the maximum diameter, from about 40% to about 85% of the maximum diameter, from about 40% to about 80% of the maximum diameter, from about 45% to about 75% of the maximum diameter, or from about 50% to about 70% of the maximum diameter, such as, for example, about 45% of the maximum diameter, about 50% of the maximum diameter, about 55% of the maximum diameter, about 60% of the maximum diameter, about 65% of the maximum diameter, or about 70% of the maximum diameter.

The maximum diameter and the minimum diameter can be separated by any suitable distance, such as, for example, by about 5 mm, about 10 mm, about 15 mm, about 20 mm, about 25 mm, about 30 mm, about 35 mm, about 40 mm, about 45 mm, about 50 mm, or any other suitable distance.

The pessary devices can have any suitable length, such as, for example, a length from about 35 mm to about 60 mm, about 40 mm to about 55 mm, or about 40 mm to about 50 mm, such as, for example, a length about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, or about 50 mm. The length is typically measured substantially parallel to the longitudinal axis of the pessary device.

Generally, the pessary device can have a weight of less than about 10 grams, less than about 9 grams, less than about 8 grams, less than about 7 grams, less than about 6 grams, less than about 5 grams, less than about 4 grams, less than about 3 grams, less than about 2 grams, or about 1 gram, including for example, a weight of from about 1 gram to about 7 grams, or from about 2 grams to about 6 grams, or from about 3 grams to about 5 grams.

Pessary devices can be fabricated using any suitable materials and methods. For example, pessaries can be formed from polymeric materials, such as, for example, polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, or metallic materials. In certain embodiments, the pessary devices are not formed from absorbent material such as, for example, fibrous material or absorbent foam.

Pessary devices can be formed in any suitable manner, such as, for example, using injection molding, blowmolding, or other suitable methods of forming the pessary device. Pessary devices can be assembled by snap fitting two or more pieces together.

The pessary device can have one or more protuberances inside the hollow interior. The pessary device can have a plurality of protuberances. Protuberances can be integral or non-integral to the pessary device. Non-integral protuberances can be attached to the inner walls of the pessary device by any means commonly known to one of ordinary skill in the art including, such as, for example, adhesives and/or heat. Protuberances can be in the shape of a nub, a hook, a disc, a rod, triangle, pyramid, and/or any volumetric shape.

A protuberance can be used to cross an external opening to the pessary device. A protuberance can be used to connect one side of the hollow interior to the opposite side of the hollow interior crossing the longitudinal axis. One or more protuberances can form a bridge crossing the longitudinal axis. Two or more protuberances can meet at the longitudinal axis. Two or more protuberances can meet at a point between the longitudinal axis and the inner wall along the transverse axis. Protuberances can be located at different points along the longitudinal axis.

Two or more protuberances can meet and interlock within the hollow interior by any method known, such as, for example, by lock and key, hooking parts, ball and socket, and/or friction. Two or more protuberances can be symmetrical to each other within the hollow interior along one or both of the longitudinal and/or transverse axis.

Protuberances can be made from polymeric materials, such as, for example, polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, or metallic materials.

The pessary device can be covered by an overwrap. The overwrap can be non-absorbent or absorbent and can include any suitable material, such as, for example, a fibrous nonwoven material comprising natural, synthetic, or a blend of natural and synthetic fibers. Suitable synthetic fibers can include, e.g., fibers such as polyester, polyolefin, nylon, polypropylene, polyethylene, polyacrylic, cellulose acetate, polyhydroxyalkanoates, aliphatic ester polycondensates, bicomponent fibers and/or mixtures thereof. Natural fibers can include, e.g., rayon and those commonly known to be non-synthetic and of natural origin such as cotton. The fibers can have any suitable cross-sectional shape, such as, e.g., round, tri-lobal, multi-lobal, delta, hollow, ribbon-shaped, and/or any other suitable shape, or mixtures thereof. Fibers with any suitable diameter can be used, such as, e.g., from about 0.5 to about 50 microns, such as, e.g., from about 1 to about 30 microns, such as, e.g., from about 10 to about 25 microns. Fiber diameter can be determined using any suitable means; however, for non-round fibers, diameter can typically be determined by reference to the diameter of a fiber with the same cross-sectional area as the non-round fiber.

The overwrap can be made by any number of suitable techniques and can have any suitable basis weight. Suitable techniques include, for example, carding, meltblowing, spunbonding, spunlacing, airlaying, and the like. For example, the overwrap can be formed using bonding methods, such as, e.g., thermal, ultrasonic, resin, through-air bonding, hydroentangling, and/or needling. The basis weight of the overwrap can be any suitable weight, such as, e.g., from about 10 to about 60 grams per square meter (gsm), such as, e.g., from about 15 to about 30 gsm. In addition, the overwrap can be hydrophilic or hydrophobic.

The overwrap can be joined to the pessary device by any variety of means. The overwrap can be joined to itself or to the pessary device. For example, one portion of overwrap can be joined to an opposed portion of the overwrap or to the pessary device using any suitable adhesive or heat pressure bonding means. Such adhesive can extend continuously along the length of attachment or it can be applied in a non-continuous fashion at discrete intervals. Heat bonding includes thermally bonding, fusion bonding, or any other suitable means for joining such materials.

The pessary device can include a withdrawal assembly.

The intravaginal device can be inserted using an applicator that can include an insertion member and a plunger. The insertion member can have an insertion end and a withdrawal end opposite the insertion end. The insertion member also can include a barrel region adapted to contain the intravaginal device, and a grip region that can be an indentation region provided opposite the insertion end, such as, e.g., proximal to the withdrawal end.

The insertion member and/or plunger can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, poly hydroxyalkanoate, ethylene vinyl acetate, polyurethane, silicone, derivatives thereof, copolymers thereof, mixtures thereof, or any suitable smooth plastic material. Examples of suitable materials are disclosed in, e.g., U.S. Pat. Nos. 5,346,468 and 5,558,631. Additives can be included in the material to alter or enhance certain material properties. Suitable additives include, for example, mold release agents, slip agents, surface energy modifiers, pearlescent agents, and/or any other suitable additives. The insertion member also or alternatively can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the insertion member can include a textured surface. Texture can be provided in any suitable manner, such as, e.g., by designing texture into or adding texture to the insertion member.

The insertion member can include a grip region, such as, for example, an indentation region. The grip region can have a plurality of three-dimensional surface elements, such as, e.g., projections, rings, ridges, ribs, embossments, depressions, grooves, and/or other gripping structures. The three-dimensional surface elements can be provided in any suitable manner, such as, e.g., by the addition of material, and/or by impressing, such as, e.g., by embossing, or compressing the surfaces. For example, the indentation region can include one or more flattened sides and/or one or more spaces for a decorative marking or a character, such as, e.g., an embossed and/or printed marking or character. In addition, or alternatively, the surfaces of the indentation region can include a material that can provide a frictional resistance for the user's fingers during the insertion of the applicator into the body. Suitable materials that can provide friction include, for example, abrasive materials, high wet coefficient of friction materials, pressure sensitive adhesives, or any combinations thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An intravaginal device comprising a body with a hollow interior, an aperture to the hollow interior, and a withdrawal assembly; wherein the withdrawal assembly comprises a withdrawal member and an obstruction that at least partially blocks the aperture; wherein the withdrawal member crosses through the aperture to the hollow interior; and wherein a portion of the withdrawal member and a portion of the obstruction are in direct contact.

2. The intravaginal device of claim 1, wherein the withdrawal assembly comprises part of an outer profile of the intravaginal device.

3. The intravaginal device of claim 1, wherein the obstruction has a non-expanded shape and an expanded shape.

4. The intravaginal device of claim 1, wherein the obstruction comprises one or more interconnected parts.

5. The intravaginal device of claim 1, wherein the intravaginal device hollow interior comprises a transverse axis and a longitudinal axis; wherein the obstruction comprises an outer length, an outer height, and an outer width; and wherein the obstruction outer length, obstruction outer width, or obstruction outer height, is greater than the smallest dimension of a transverse axis area along the longitudinal axis.

6. The intravaginal device of claim 1, wherein the obstruction comprises an outer length, an outer height, and an outer width; and wherein at least one of the obstruction outer length, obstruction outer width, or obstruction outer height, is greater than the largest dimension of the intravaginal device aperture.

7. The intravaginal device of claim 1, wherein the obstruction is part of the withdrawal member.

8. The intravaginal device of claim 1, wherein the withdrawal assembly obstruction is formed onto the withdrawal member.

9. The intravaginal device of claim 1, wherein the intravaginal device comprises a protuberance; wherein the obstruction is contained in the hollow interior by the protuberance.

10. A pessary device having a top, a base, a length, a longitudinal axis, a hollow interior, an aperture to the hollow interior, and a withdrawal assembly; wherein the withdrawal assembly comprises a withdrawal member and an obstruction, wherein the withdrawal member crosses through the aperture to the hollow interior, and wherein a portion of the withdrawal member and a portion of the obstruction are in direct contact.

11. The pessary device of claim 10, wherein the withdrawal assembly comprises part of an outer profile of the pessary device.

12. The pessary device of claim 10, wherein the obstruction has a compressed shape and an expanded shape.

13. The pessary device of claim 10, wherein the obstruction comprises one or more interconnected parts.

14. The pessary device of claim 10, wherein the pessary device hollow interior comprises a transverse axis and a longitudinal axis; wherein the obstruction comprises an outer length, an outer height, and an outer width; and wherein at least one of the obstruction outer length, obstruction outer width, or obstruction outer height, is greater than the smallest dimension of a transverse axis area along the longitudinal axis.

15. The pessary device of claim 10, wherein the obstruction comprises an outer length, an outer height, and an outer width; and wherein at least one of the obstruction outer length, obstruction outer width, or obstruction outer height, is greater than the largest dimension of the aperture.

16. The pessary device of claim 10, wherein the obstruction is part of the withdrawal member.

17. The pessary device of claim 10, wherein the withdrawal assembly obstruction is formed onto the withdrawal member.

18. The pessary device of claim 10, wherein the pessary device comprises a protuberance and wherein the obstruction is contained in the hollow interior by the protuberance.

19. A pessary device having a top, a base, a length, a longitudinal axis, a transverse axis, a hollow interior, an aperture to the hollow interior, and a withdrawal assembly; wherein the withdrawal assembly comprises a withdrawal member and an obstruction; wherein a portion of the withdrawal member and a portion of the obstruction are in direct contact; wherein the obstruction comprises an outer length, an outer height, and an outer width; wherein at least one of the obstruction outer length, obstruction outer width, or obstruction outer height, is greater than the smallest dimension of a transverse axis area along the longitudinal axis; wherein the withdrawal member crosses through the aperture to the hollow interior; and wherein at least one of the obstruction outer length, obstruction outer width, or obstruction outer height, is greater than the largest dimension of the aperture.

* * * * *